United States Patent
Haas et al.

(10) Patent No.: US 6,608,219 B2
(45) Date of Patent: Aug. 19, 2003

(54) PROCESS FOR THE EPOXIDATION OF OLEFINS

(75) Inventors: Thomas Haas, Frankfurt (DE); Willi Hofen, Rodenbach (DE); Georg Thiele, Hanau (DE); Stefan Pilz, Ulm (DE); Wolfgang Woell, Maintal (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 0 days.

(21) Appl. No.: 10/170,203

(22) Filed: Jun. 13, 2002

(65) Prior Publication Data

US 2003/0009040 A1 Jan. 9, 2003

Related U.S. Application Data

(60) Provisional application No. 60/297,509, filed on Jun. 13, 2001.

(51) Int. Cl.$^7$ .............................................. C07D 301/12
(52) U.S. Cl. ...................................... 549/531; 549/524
(58) Field of Search ................................ 549/531, 524

(56) References Cited

U.S. PATENT DOCUMENTS

| | | |
|---|---|---|
| 2,870,171 A | 1/1959 | Gable |
| 4,410,501 A | 10/1983 | Taramasso et al. |
| 4,833,260 A | 5/1989 | Neri et al. |
| 5,523,426 A | 6/1996 | Jubin, Jr. et al. |
| 5,591,875 A | 1/1997 | Chang et al. |
| 5,599,955 A | 2/1997 | Vora et al. |
| 5,620,935 A | 4/1997 | Thiele |
| 5,675,026 A | 10/1997 | Thiele |
| 5,760,253 A | 6/1998 | Danner et al. |
| 5,849,937 A | 12/1998 | Jubin, Jr. et al. |
| 5,849,938 A | 12/1998 | Rueter et al. |
| 5,912,367 A | 6/1999 | Chang |
| 6,042,807 A | 3/2000 | Faraj |
| 6,063,941 A | 5/2000 | Gilbeau |
| 6,372,924 B2 | 4/2002 | Thiele |

FOREIGN PATENT DOCUMENTS

| | | |
|---|---|---|
| DE | 196 23 611 | 12/1997 |
| DE | 197 23 950 A1 | 12/1998 |
| DE | 197 54 185 | 2/1999 |
| DE | 198 35 907 | 2/2000 |
| EP | 0 100 118 | 2/1984 |
| EP | 0 100 119 A1 | 2/1984 |
| EP | 0 106 671 | 4/1984 |
| EP | 0 230 349 | 7/1987 |
| EP | 0 230 949 A3 | 8/1987 |
| EP | 0 568 336 | 11/1993 |
| EP | 0 568 337 | 11/1993 |
| EP | 0 583 828 | 2/1994 |
| EP | 0 645 473 A1 | 3/1995 |
| EP | 0 659 473 | 6/1995 |
| EP | 0 712 852 | 5/1996 |
| EP | 0 719 768 | 7/1996 |
| EP | 0 757 045 | 2/1997 |
| EP | 0 795 537 A1 | 9/1997 |
| EP | 0 827 765 | 3/1998 |
| EP | 0 930 308 | 7/1999 |
| EP | 0 936 219 | 8/1999 |
| EP | 1 066 711 A1 | 1/2001 |
| EP | 1 122 248 | 8/2001 |
| EP | 1 138 387 | 10/2001 |
| EP | 1 221 442 | 7/2002 |
| JP | 2166636 | 6/1990 |
| WO | WO 97/47613 | 12/1997 |
| WO | WO 97/47614 | 12/1997 |
| WO | WO 99/01445 | 1/1999 |
| WO | WO 99/07690 | 2/1999 |
| WO | WO 99/11639 | 3/1999 |
| WO | WO 00/07965 | 2/2000 |
| WO | WO 00/17178 | 3/2000 |

OTHER PUBLICATIONS

European Search Report, dated May 23, 2001, 3 pps.

*Primary Examiner*—Ba K. Trinh
(74) *Attorney, Agent, or Firm*—Smith, Gambrell & Russell, LLP

(57) ABSTRACT

A process for the catalytic epoxidation of olefins with hydrogen peroxide in a multiphase reaction mixture comprising a liquid aqueous hydrogen peroxide rich phase containing an organic solvent having a solubility in water of at least 10% by weight at 25° C. and a liquid organic olefin rich phase.

21 Claims, No Drawings

PROCESS FOR THE EPOXIDATION OF OLEFINS

REFERENCE TO A RELATED APPLICATION

This application claims the benefit of provisional application No. 60/297,509 filed Jun. 13, 2001 which is relied on and incorporated herein by reference.

INTRODUCTION AND BACKGROUND

The present invention relates to a process for the catalytic epoxidation of olefins with hydrogen peroxide in a multiphase reaction mixture comprising a liquid aqueous hydrogen peroxide rich phase containing an organic solvent having a solubility in water of at least 10% by weight at 25° C. and a liquid organic olefin rich phase.

From EP-A 100 119 and EP-A 230 949 it is known that propene can be converted by hydrogen peroxide into propene oxide if a titanium-containing zeolite is used as catalyst.

Unreacted hydrogen peroxide cannot be recovered economically from the epoxidation reaction mixture. Furthermore, unreacted hydrogen peroxide involves additional effort and expenditure in the working up of the reaction mixture. The epoxidation of propene is therefore preferably carried out with an excess of propene and up to a high hydrogen peroxide conversion. In order to achieve a high hydrogen peroxide conversion it is advantageous to use a continuous flow reaction system. Such a reaction system may comprise either one or more continuous flow reactors or an arrangement of two or more flow mixing reactors connected in series. Examples of flow mixing reactors are stirred tank reactors, recycle reactors, fluidised bed reactors and fixed bed reactors with recycling of the liquid phase.

Hydrogen peroxide is in general applied in the epoxidation reaction as aqueous solution. Thus it is believed that the epoxidation reaction takes place in the liquid aqueous phase. Therefore in order to achieve a high reaction velocity as high a propene concentration as possible in the liquid phase is necessary. Since the liquid phase predominantly comprises aqueous hydrogen peroxide solution and optionally an organic solvent solubility of propene in the aqueous phase is limited. So far in the prior art two different routes are described to achieve a high propene concentration in the aqueous phase.

Since it is generally known that diffusion in a gas phase is by several magnitudes faster compared to diffusion in a liquid phase (see for example Perry's Chemical Engineers' Handbook, $7^{th}$ edition, Mc Graw.Hill, 1997, pp 5–42) the reaction is carried out under a propene atmosphere at elevated pressure with the effect that a reaction system with an aqueous phase comprising all of the hydrogen peroxide and some propene and a propene rich gas phase is present. Thereby propene depleted from the liquid phase due to reaction is supplemented by propene from the gas phase.

From EP-A 100 119 and EP-A 230 949 it is known that in the epoxidation reaction a solvent can be used to improve the solubility of propene in the aqueous peroxide phase. In accordance with the above described theory the reaction is conducted at elevated pressure to increase the solubility of propene in the aqueous phase. Only if no solubilizing solvent is present the increased pressure would lead to a liquidification of propene. The presence of an organic propene rich phase in case of an aqueous phase containing a solubilizing solvent is not disclosed.

A similar route is taken in WO 99/01445 teaching a process for epoxidation of propene wherein temperature and pressure is increased during operation of the reactor in a manner effective to maintain a substantially constant concentration of propene in the liquid aqueous phase in order to compensate for catalyst deactivation. As is evident from examples 1 and 2 in WO 99/01445 the temperature is increased during the course of reaction from 65.6° C. to 71.1° C. in order to maintain a constant $H_2O_2$ conversion to compensate for catalyst deactivation. In example 1 the pressure was held approximately constant at about 20 bar with the result that concentration of propene in the aqueous phase and propene oxide selectivity decreased. In contrast thereto in example 2 the pressure was increased to hold the propene concentration approximately constant with the result that propene oxide selectivity decreased to a lesser extent. But it would be still desirable to achieve a better propene oxide selectivity.

EP-A 659 473 describes an epoxidation process wherein according to the examples a liquid mixture of hydrogen peroxide, isopropanol as solvent and propene is led over a succession of fixed bed reaction zones connected in series in down-flow operation. In each reaction zone the reaction is performed to a partial conversion, the liquid reaction mixture is removed from each reaction zone, is led over an external heat exchanger to extract the heat of reaction, and the major proportion of this liquid phase is then recycled to this reaction zone and a minor proportion of the liquid phase is passed to the next zone. Thus each reaction zone can be considered as an independent adiabatic reactor. At the same time gaseous propene is fed in together with the liquid feed stock mixture, is guided in a parallel stream to the liquid phase over the fixed bed reaction zones, and is extracted at the end of the reaction system in addition to the liquid reaction mixture as an oxygen-containing waste gas stream. As is evident from the examples reaction conditions were chosen that result in only one liquid aqueous phase wherein propene is dissolved. The increase in propene oxide yield compared to conventional tubular reactors is only related to the temperature control described in EP-A 659 473. But on account of the complexity of the reaction system required to carry out the process considerable additional costs are involved.

Similarly according to WO 00/07965 the epoxidation reaction is conducted under conditions to have only one phase i.e. the liquid aqueous phase having a reasonably high propene concentration. In example 2 an aqueous hydrogen peroxide solution, methanol and propene is fed to a fixed bed tubular reactor. By adjusting the relative amounts of the feeds to a low ratio of propene feed to total feed and a high ratio of methanol feed to total feed and by applying a pressure of 20 bar only one liquid phase is present. Although by taking this measures a hydrogen peroxide conversion of 98.4% could be achieved the propene oxide selectivity of 80.3% is still too low for a commercial application of the described process.

DE 197 23 950 is very similar to WO 00/07965. There is disclosed in DE 197 23 950 that the reaction may be conducted in a homogenous phase or in a multiphase system, for example, a two-phase system but there is no disclosure of the presence of an aqueous liquid phase and an organic liquid phase.

In WO 00/17178 as an alternative the possibility of conducting the epoxidation of propene with hydrogen peroxide using two liquid phases i.e. an aqueous phase and an organic phase is disclosed. But the presence of organic solvents having a low solubility in water like halogenated hydrocarbons are described as mandatory in order to form a second organic phase. Thus the second liquid organic phase is formed by a water insoluble organic solvent.

In view of the cited prior art it is an object of the present invention to provide a process for the epoxidation of olefines that results in improved product selectivity compared to WO 00/07965 which can be carried out using conventional reaction systems.

SUMMARY OF THE INVENTION

The above and other objects of the invention can be achieved by a process for the catalytic epoxidation of olefins with hydrogen peroxide in a multiphase reaction mixture comprising a liquid aqueous hydrogen peroxide rich phase containing an organic solvent having a solubility in water of at least 10% by weight at 25° C. and a liquid organic olefin rich phase.

According to a preferred embodiment the present invention refers to a process for the epoxidation of propene with hydrogen peroxide in the presence of a titanium-containing zeolite as the catalyst in a multiphase reaction mixture comprising a liquid aqueous hydrogen peroxide rich phase containing methanol and dissolved propene and a liquid organic propene rich phase.

The present inventors have surprisingly discovered that by using a multiphase reaction mixture comprising a liquid aqueous hydrogen peroxide rich phase and a liquid organic olefin rich phase product selectivity compared to the prior art can be considerably improved without compromising hydrogen peroxide conversion. This result was especially surprising since it was expected from general textbook knowledge as exemplified by Perry's Chemical Engineers' Handbook supra, that in case of two liquid phases mass transfer from the liquid organic phase to the liquid aqueous phase where the reaction takes place should be by magnitudes slower compared to systems having a single aqueous phase or an aqueous phase and an olefin gas phase. According to the expectations this should have a negative effect on hydrogen peroxide conversion. But nevertheless product selectivity could be successfully improved according to the present invention without compromising conversion.

DETAILED DESCRIPTION OF THE INVENTION

The essential feature of the present invention is the presence of two immiscible liquid phases; i.e a liquid aqueous hydrogen peroxide rich phase and a liquid organic olefin rich phase while having a water miscible organic solvent present in the aqueous phase. As will be appreciated by any person skilled in the art the presence of two immiscible phases in a reaction system comprising an olefin, a water miscible organic solvent and an aqueous hydrogen peroxide solution will depend on many different factors.

First of all, the presence of an additional olefin rich liquid organic phase will depend on the temperature and pressure applied in the reactor and the selected olefin. Preferably, the applied pressure is at or above the vapor pressure of the olefin at the chosen temperature. Furthermore it will depend on the selection of the organic solvent.

Suitable as organic solvents are all solvents that are not oxidized or are oxidized only to a slight extent by hydrogen peroxide under the chosen reaction conditions, and that dissolve in an amount of more than 10 wt. % in water at 25° C. Preferred are solvents that dissolve in an amount of more than 30 wt. % in water at 25° C. preferably more than 50 wt. % in water at 25° C. The most preferred solvents are completely miscible with water. Suitable solvents include alcohols such as methanol, ethanol or tert.-butanol; glycols such as for example ethylene glycol, 1,2-propanediol or 1,3-propanediol; cyclic ethers such as for example tetrahydrofuran, dioxane or propylene oxide; glycol ethers such as for example ethylene glycol monomethyl ether, ethylene glycol monoethyl ether, ethylene glycol monobutyl ether or propylene glycol monomethyl ether, and ketones such as for example acetone or 2-butanone. Methanol is particularly preferred.

Using the process according to the invention any olefin can be epoxidized; in particular olefins with 2 to 6 carbon atoms. The process according to the invention is most particularly suitable for the epoxidation of propene to propene oxide. For economic reasons it would be preferred for an industrial scale process to use propene, not in a pure form, but as a technical mixture with propane that as a rule contains 1 to 15 vol. % of propane.

Additionally the presence of a second organic olefin rich phase will depend on the relative amounts of olefin, water and solvent. The amount of solvent is chosen to achieve sufficient solubility of the olefin in the hydrogen peroxide rich aqueous phase in order to get the desired rate of reaction. At a given temperature, pressure, olefin and solvent, the relative amounts of ingredients can be adjusted to ensure formation of a second liquid organic phase. That is, to ensure the formation of a second liquid organic olefin rich phase the amount of olefin has to be selected in excess of the amount soluble in the aqueous phase at the chosen temperature and pressure.

A simple means of experimentally confirming the presence of a second liquid organic phase at the reaction conditions is by collecting a sample of the reaction mixture in a container equipped with a sight glass at the temperature and pressure used in the process. Alternatively, the reactor may be equipped with a sight glass at a suitable position to observe the phase boundary directly during the reaction. In case of a continuous flow reactor the sight glass is preferably positioned near the outlet of the reactor effluent to have an optimal control that two liquid phases are present through out the entire residence time within the reactor.

Thus a person skilled in the art can without any effort verify whether when applying certain selections for olefins, solvents and reaction parameters a two-liquid phase system as required by the present invention is present and can adjust by variation of the parameters as discussed above in detail the reaction system in order to establish a second liquid organic phase.

According to a most preferred embodiment of the present invention the olefin is selected to be propene, and methanol is used as a solvent. For example for a reaction mixture comprising propene, methanol, and aqueous hydrogen peroxide at a reaction temperature between 30° C. and 80° C., a pressure from 5 to 50 bar the ratio of propene flow to total flow in case of a continuous flow system can be adjusted to be in the range of 0.1 to 1, preferably 0.2 to 1 in order to obtain a second liquid organic phase. Specific reaction conditions are shown in the examples.

A further advantage of a process of the present invention is, that even if the feed stream to the reactor contains olefin oxide either due to the presence of olefin oxide in the feed stream or due to partial recycling of the reactor effluent, the product selectivity is not considerably effected, although a person skilled in the art would expect that an increased concentration of product in the reaction mixture should be detrimental for product selectivity.

An additional gas phase comprising olefin vapor and optionally an inert gas; i.e. a gas that does not interfere with the epoxidation can be additionally present according to the present invention. Adding an inert gas is useful to maintain a constant pressure inside the reactor and to remove oxygen gas formed by the decomposition of a small part of the hydrogen peroxide charged to the reactor.

According to the present invention any known reaction system for the epoxidation of olefins is applicable including batch reactors and continuous flow reactors. It is preferred to use a non-adiabatic reaction system; i.e. a reaction system wherein the reaction heat is at least partially removed during the course of the reaction. Reactor systems with external or intermediate cooling are less preferred due to cost considerations. Continuous flow reaction system, especially those wherein the reaction mixture is passed through a fixed catalyst bed are particularly preferred.

In the practice of the present invention according to the above preferred embodiment any conventional reactor having a fixed catalyst bed and cooling means can be used. Preferably tubular reactors having a cooling jacket are applied since they are standardly available at relatively low cost. As cooling medium that is pumped through the cooling means, preferably the cooling jacket, preferably water is used. By preference the temperature of the cooling medium is controlled by a thermostat and the flow rate of the cooling medium is adjusted to keep the temperature difference between entry of the cooling medium into the cooling means and exit below 5° C.

In a preferred embodiment of the present invention the reaction mixture is passed through the catalyst bed in a continuous flow operation mode with a superficial velocity from 1 to 100 m/h, preferably 5 to 50 m/h, most preferred 5 to 30 m/h. The superficial velocity is defined as the ratio of volume flow rate/cross section of the catalyst bed. Consequently the superficial velocity can be varied in a given tubular reactor by adjusting the flow rate of the reaction mixture.

Additionally it is preferred to pass the reaction mixture through the catalyst bed with a liquid hourly space velocity (LHSV) from 1 to 20 $h^{-1}$, preferably 1.3 to 15 $h^{-1}$.

Whenever the flow rate of the reaction mixture is adjusted to fulfill the above defined requirements for superficial velocity and liquid hourly space velocity particularly high selectivities can be achieved. According to an especially preferred embodiment of the present invention the process is conducted in down-flow operation mode; especially where the catalyst bed is maintained in a trickle bed state.

When practicing the present invention the overall feed stream to the reactor comprises an aqueous hydrogen peroxide solution, an olefin and the organic solvent. Thereby these components may be introduced into the reactor as independent feeds or one or more of these feeds are mixed prior to introduction into the reactor.

In order to be able to operate the process continuously when changing and/or regenerating the epoxidation catalyst, two or more reactors may if desired also be operated in parallel or in series in the aforedescribed manner.

Crystalline, titanium-containing zeolites especially those of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501. The titanium silicalite catalyst may be employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

The hydrogen peroxide is used in the process according to the invention in the form of an aqueous solution with a hydrogen peroxide content of 1 to 90 wt. %, preferably 10 to 70 wt. % and particularly preferably 30 to 50 wt. %. The hydrogen peroxide may be used in the form of the commercially available, stabilized solutions. Also suitable are unstabilized, aqueous hydrogen peroxide solutions such as are obtained in the anthraquinone process for producing hydrogen peroxide.

The process according to the invention for the epoxidation of olefins, preferably propene, is typically carried out at a temperature of 30° to 80° C., preferably at 40° to 60° C. According to a particularly preferred embodiment of the present invention a temperature profile within the reactor in maintained such that the cooling medium temperature of the cooling means, preferably the cooling liquid in the cooling jacket of the tubular reactor is at least 40° C. and the maximum temperature within the catalyst bed is 60° C. at the most. By selecting such a narrowly defined temperature profile within the reactor an optimized balance between hydrogen peroxide conversion and olefin oxide selectivity can be achieved.

The pressure within the reactor is usually maintained at a pressure at or above the vapor pressure of the olefin at the selected temperature for example at 10 to 50 bar, preferably at 20 to 50, most preferred 21 to 30 bar. With propene this translates to a pressure of at least 16.5 bar at a reaction temperature of 40° C. and at least 25 bar at a reaction temperature of 60° C.

The olefin is preferably employed in excess relative to the hydrogen peroxide and in an amount sufficient to maintain a second liquid olefin rich phase during the reaction. The molar ratio of olefin, preferably propene, to hydrogen peroxide preferably being chosen in the range from 1.1 to 30. The solvent is preferably added in a weight ratio of 0.5 to 20 relative to the amount of hydrogen peroxide solution used. The amount of catalyst employed may be varied within wide limits and is preferably chosen so that a hydrogen peroxide consumption of more than 90%, preferably more than 95%, is achieved within 1 minute to 5 hours under the employed reaction conditions.

The present invention refers to a process for the catalytic epoxidation of olefins with hydrogen peroxide in a multiphase reaction mixture comprising a liquid aqueous hydrogen peroxide rich phase containing an organic solvent having a solubility in water of at least 10% by weight at 25° C. and a liquid organic olefin rich phase.

Preferably, the organic solvent has a solubility in water of at least 30% by weight, preferably at least 50% by weight at 25° C.

According to the present invention the following are preferred conditions:
the solvent has unlimited solubility in water at 25° C.;
a continuous flow reaction system is employed;
a fixed bed reactor comprising cooling means is use;
the reactor is tubular and the cooling means is a cooling jacket;
the epoxidation is conducted in down-flow operation mode; and
the fixed catalyst bed is maintained in a trickle bed state.

Further, it is preferred that the reaction mixture is passed through the catalyst bed with a superficial velocity from 1 to 100 m/h, more preferably 5 to 50 m/h, and most preferably 5 to 30 m/h.

In addition, it is preferred that the reaction mixture is passed through the catalyst bed with a liquid hourly space velocity (LHSV) from 1 to 20 $h^{-1}$, more preferably 1.3 to 15 $h^{-1}$.

The reaction temperature conditions are preferably from 30 to 80° C., more preferably from 40 to 60° C. A temperature profile within the reactor in maintained, according to preferred conditions, such that the cooling medium temperature of the cooling means is at least 40° C. and the maximum temperature within the catalyst bed is 60° C. at the most.

Preferably, a titanium-containing zeolite is used as the catalyst.

According to a preferred embodiment the present invention refers to a process for the epoxidation of propene with hydrogen peroxide in the presence of a titanium-containing zeolite as catalyst in a multiphase reaction mixture comprising a liquid aqueous hydrogen peroxide rich phase containing methanol and dissolved propene and a liquid organic propene rich phase.

The present invention will be explained in more detail referring to the following examples:

EXAMPLES 1 AND 2 AND COMPARATIVE EXAMPLES 1

A titanium-silicate catalyst was employed in all examples. The titanium-silicate powder was shaped into 2 mm extrudates using a silica sol as binder in accordance with example 5 in EP 00 106 671.1. The $H_2O_2$ employed was prepared according to the anthraquinone process as a 40 wt-% aqueous solution.

Epoxidation is carried out continuously in down-flow operation mode in a reaction tube of 300 ml volume, a diameter of 10 mm and a length of 4 m. The reactor was additionally equipped with a sight glass located near the reactor outlet to allow visible verification whether two liquid phases were present as described above. The equipment is furthermore comprised of three containers for liquids and relevant pumps and a liquid separating vessel. The three containers for liquids comprised methanol, the 40% $H_2O_2$ and propene. The 40% $H_2O_2$ was adjusted with ammonia to a pH of 4.5. The reaction temperature was controlled via an aqueous cooling liquid circulating in a cooling jacket whereby the cooling liquid temperature is adjusted to 40° C. by a thermostat. The reactor pressure was adjusted as indicated in Table 1. Mass flow of the feeding pumps was adjusted to result in a methanol flow of 0.2 kg/h, a $H_2O_2$ flow of 0.033 kg/h. The propene flow in example 1 and comparative example 1 was adjusted to 0.0753 kg/h and to 0.125 kg/h in example 2.

COMPARATIVE EXAMPLE 2

Comparative example 1 was repeated using reaction parameters as disclosed in Example 2 of WO 00/07965 and reported in Table 1.

The product stream was analyzed by gas chromatography and the $H_2O_2$ conversion was determined by titration. Propene selectivity was calculated as the ratio of the amount of propene oxide relative to the total amount of propene oxide and oxygen containing hydrocarbons formed during the epoxidation reaction such as 1-methoxy-2-propanol, 2-methoxy-1-propanol and 1,2-propanediol. The results are given in Table 1.

TABLE 1

| No. | Pressure [bar] | Number of liquid phases in the effluent | Ratio $Flow_{propene}$ $Flow_{total}$ | $H_2O_2$ Conversion [%] | Propene Oxide Selectivity [%] | Propene Oxide Yield based on $H_2O_2$ [%] |
|---|---|---|---|---|---|---|
| E1 | 25 | 2 | 0.21 | 96 | 96 | 92 |
| E2 | 25 | 2 | 0.35 | 96 | 97 | 93 |
| CE1 | 15 | 1 | 0.21 | 95 | 88 | 84 |
| CE2 | 20 | 1 | 0.12 | 98 | 80 | 78 |

As can be seen from the experimental results conducting the epoxidation reaction in the presence of two liquid phases according to the present invention results in an considerable increase in propene oxide selectivity without compromising hydrogen peroxide conversion compared to the prior art. Thus high propene oxide yields can be obtained with the process of the present invention.

Further modifications and variations will be apparent to those skilled in the art from the foregoing and are intended to be encompassed by the claim appended hereto.

What is claimed is:

1. A process for the catalytic epoxidation of olefins with hydrogen peroxide in a multiphase reaction mixture comprising reacting a liquid aqueous hydrogen peroxide rich phase containing an organic solvent having a solubility in water of at least 10% by weight at 25° C. and a liquid organic olefin rich phase.

2. The process of claim 1, wherein the organic solvent has a solubility in water of at least 30% by weight at 25° C.

3. The process of claim 1, wherein the organic solvent has a solubility in water of at least 50% by weight at 25° C.

4. The process of claim 1, wherein the solvent has unlimited solubility in water at 25° C.

5. The process of claim 1, wherein the reaction takes place in a continuous flow reaction system.

6. The process of claim 5, wherein said reaction system is a fixed bed reactor comprising cooling means.

7. The process of claim 5, wherein the reactor is tubular and the cooling means is a cooling jacket.

8. The process of claim 5, wherein the epoxidation is conducted in down-flow operation mode.

9. The process of claim 6, wherein the epoxidation is conducted in down-flow operation mode.

10. The process of claim 8, wherein the fixed catalyst bed is maintained in a trickle bed state.

11. The process of claim 9, wherein the fixed catalyst bed is maintained in a trickle bed state.

12. The process of claim 6, wherein the reaction mixture is passed through the catalyst bed with a superficial velocity from 1 to 100 m/h.

13. The process of claim 6, wherein the reaction mixture is passed through the catalyst bed with a superficial velocity from 5 to 50 m/h.

14. The process of claim 6, wherein the reaction mixture is passed through the catalyst bed with a superficial velocity from 5 to 30 m/h.

15. The process of claim 6, wherein the reaction mixture is passed through the catalyst bed with a liquid hourly space velocity (LHSV) from 1 to 20 $h^{-1}$.

16. The process of claim 6, wherein the reaction mixture is passed through the catalyst bed with a liquid hourly space velocity (LHSV) from 1.3 to 15 $h^{-1}$.

17. The process of claim 1, wherein the reacting takes place at a reaction temperature of from 30 to 80° C.

18. The process of claim 1, wherein the reacting takes place at a reaction temperature of from 40 to 60° C.

19. The process of claim 18, further comprising maintaining a temperature profile within the reactor such that the cooling medium temperature of the cooling means is at least 40° C. and the maximum temperature within the catalyst bed is 60° C. at most.

20. The process of claim 1, wherein a titanium-containing zeolite is present as catalyst.

21. A process for the epoxidation of propene comprising reacting propene with hydrogen peroxide in the presence of a titanium-containing zeolite as catalyst in a multiphase reaction mixture comprising a liquid aqueous hydrogen peroxide rich phase containing methanol and dissolved propene and a liquid organic propene rich phase.

* * * * *